United States Patent
Gallem et al.

(10) Patent No.: US 7,891,352 B2
(45) Date of Patent: Feb. 22, 2011

(54) AEROSOL GENERATING MEANS FOR INHALATION THERAPY DEVICES

(75) Inventors: Thomas Gallem, Munich (DE); Norbert Kamm, Munich (DE); Joseph Lass, Munich (DE); Gerhard Pumm, Oberau (DE); Roland Stangl, Moosburg (DE)

(73) Assignee: PARI Pharma GmbH, Starnberg (DE)

( * ) Notice: Subject to any disclaimer, the term of this patent is extended or adjusted under 35 U.S.C. 154(b) by 916 days.

(21) Appl. No.: 11/346,001

(22) Filed: Feb. 2, 2006

(65) Prior Publication Data
US 2006/0207591 A1   Sep. 21, 2006

(30) Foreign Application Priority Data
Feb. 11, 2005   (DE)   ........... 10 2005 006 375

(51) Int. Cl.
*A61M 11/00*   (2006.01)
(52) U.S. Cl. ................................. 128/200.14
(58) Field of Classification Search ............ 128/200.14, 128/200.16
See application file for complete search history.

(56) References Cited

U.S. PATENT DOCUMENTS

| | | | | |
|---|---|---|---|---|
| 5,518,179 A | * | 5/1996 | Humberstone et al. | ... 239/102.2 |
| 5,657,926 A | * | 8/1997 | Toda | ........... 239/102.2 |
| 5,823,428 A | * | 10/1998 | Humberstone et al. | ......... 239/4 |
| 6,062,212 A | * | 5/2000 | Davison et al. | ........ 128/200.16 |
| 6,293,474 B1 | * | 9/2001 | Helf et al. | ................ 239/102.2 |
| 6,843,430 B2 | * | 1/2005 | Boticki et al. | ............ 239/102.1 |
| 6,948,491 B2 | * | 9/2005 | Loeffler et al. | ......... 128/200.14 |

FOREIGN PATENT DOCUMENTS

| | | |
|---|---|---|
| EP | 0 615 470 B1 | 12/1995 |
| EP | 0615470 B1 * | 12/1995 |

\* cited by examiner

*Primary Examiner*—Steven O Douglas
(74) *Attorney, Agent, or Firm*—Wolf, Greenfield & Sacks, P.C.

(57) ABSTRACT

The invention describes an aerosol generator for inhalation therapy devices, in which an oscillatable assembly, consisting of at least a membrane and an oscillation generator, is mounted in an encapsulating means such that at least the membrane is exposed for the supply of liquid and the generation of an aerosol, whereas the remaining parts of the oscillatable assembly are protected. Mounting occurs by means of a flexible passage such that the oscillatory motions of the oscillatable assembly are not negatively affected.

9 Claims, 5 Drawing Sheets

AEROSOL GENERATING MEANS FOR INHALATION THERAPY DEVICES

Figure 1:
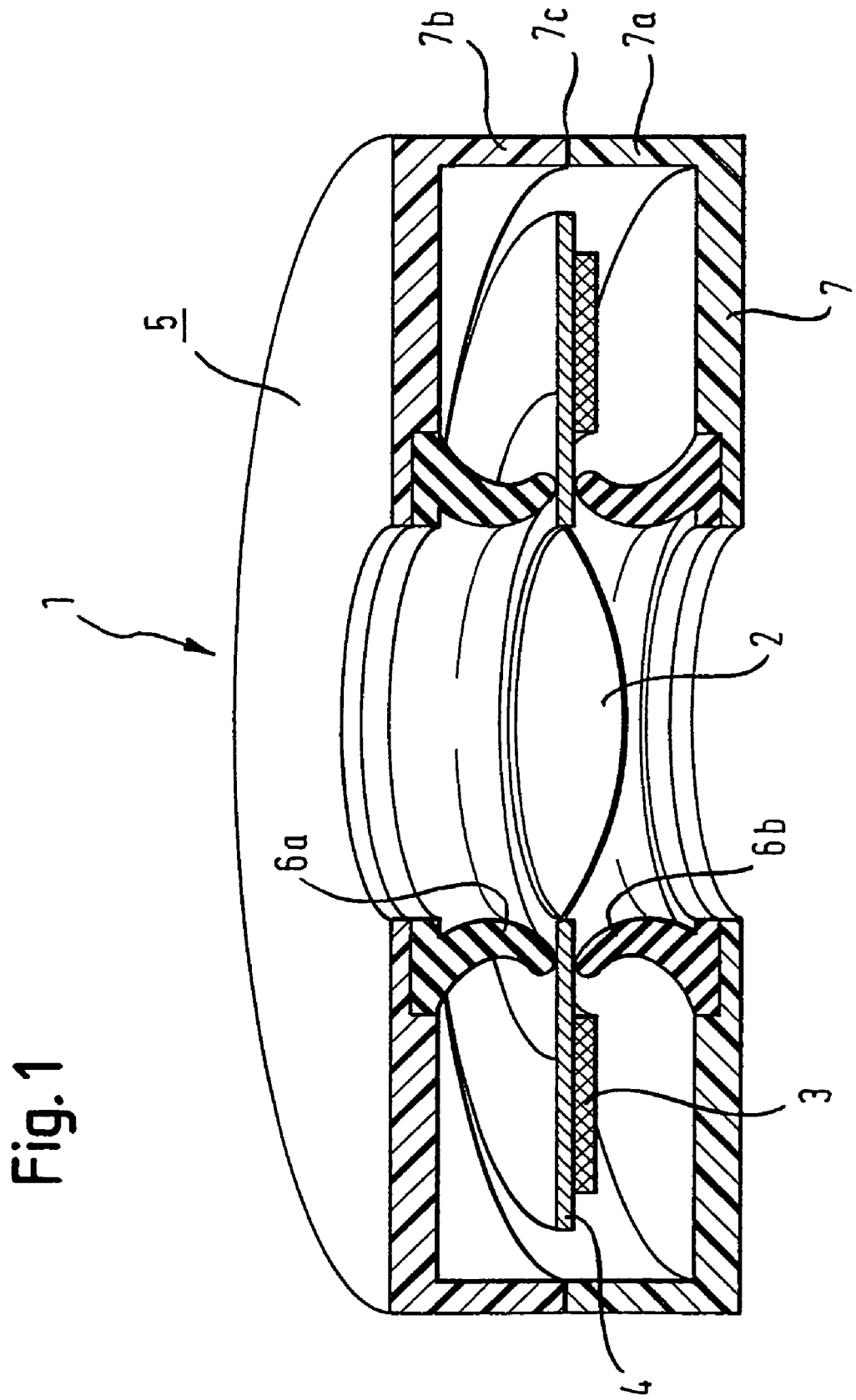

The present invention relates to an aerosol generating means for inhalation therapy devices.

Different aerosol generators are known for use in inhalation therapy devices, the object of which is to generate an aerosol from a liquid. Particularly effective aerosol generators have a membrane which is caused to oscillate by an oscillation generator in order to nebulise a supplied liquid. The oscillatable assembly of these aerosol generators is decisive for the quality of the generated aerosol and thus for dosage accuracy, however, it is at the same time also generally very sensitive. In view of the therapeutic nature of the use in inhalation therapy devices, it is, however, necessary for the aerosol generator of an inhalation therapy device to be cleaned thoroughly on a regular basis. In order to do so, the aerosol generator generally has to be removed from the inhalation therapy device and cleaned, in certain cases also autoclaved, and thus the aerosol generator is often handled by the patient/doctor.

Although the structure of the oscillatable assembly of an aerosol generator of the type discussed here is basically known, for example, from EP 0 615 470 A, there are no convincing suggestions as to how protection of the oscillatable assembly and the handleability of the aerosol generator can be improved without negatively affecting the oscillatory motions of the oscillatable assembly during aerosol generation and consequently also the quality of the aerosol and the dosage accuracy.

According to the invention, this object is achieved by means of an aerosol generating means for inhalation therapy devices, comprising an oscillatable assembly having a membrane to which a liquid can be supplied for generation of an aerosol and an oscillation generating means which causes the membrane to oscillate for generation of an aerosol, and comprising an encapsulating means for accommodating and mounting the oscillatable assembly such that parts of the oscillatable assembly are disposed in the interior of the encapsulating means and at least the membrane is exposed for supply of a liquid and generation of an aerosol, said encapsulating means having a flexible passage which contacts the oscillatable assembly.

A secure mounting of the oscillatable assembly as well as extensive protection against impurities and damage is achieved by the design according to the invention. The encapsulating means accommodates large parts of the oscillatable assembly in its interior and only leaves those regions exposed which absolutely have to be freely accessible for supply of the liquid and generation of the aerosol. Since the required passage of the encapsulating means is designed in a flexible manner according to the invention, the oscillatory motions of the oscillatable assembly are not negatively affected as a result of the mounting effected by means of the passage and the associated contact between the oscillatable assembly and the encapsulating means. The encapsulating means is optimally designed such that the passage touches the oscillatable assembly in the region of an oscillation nodal line.

The invention is explained in more detail below by means of embodiments and referring to the figures.

Figure 2:
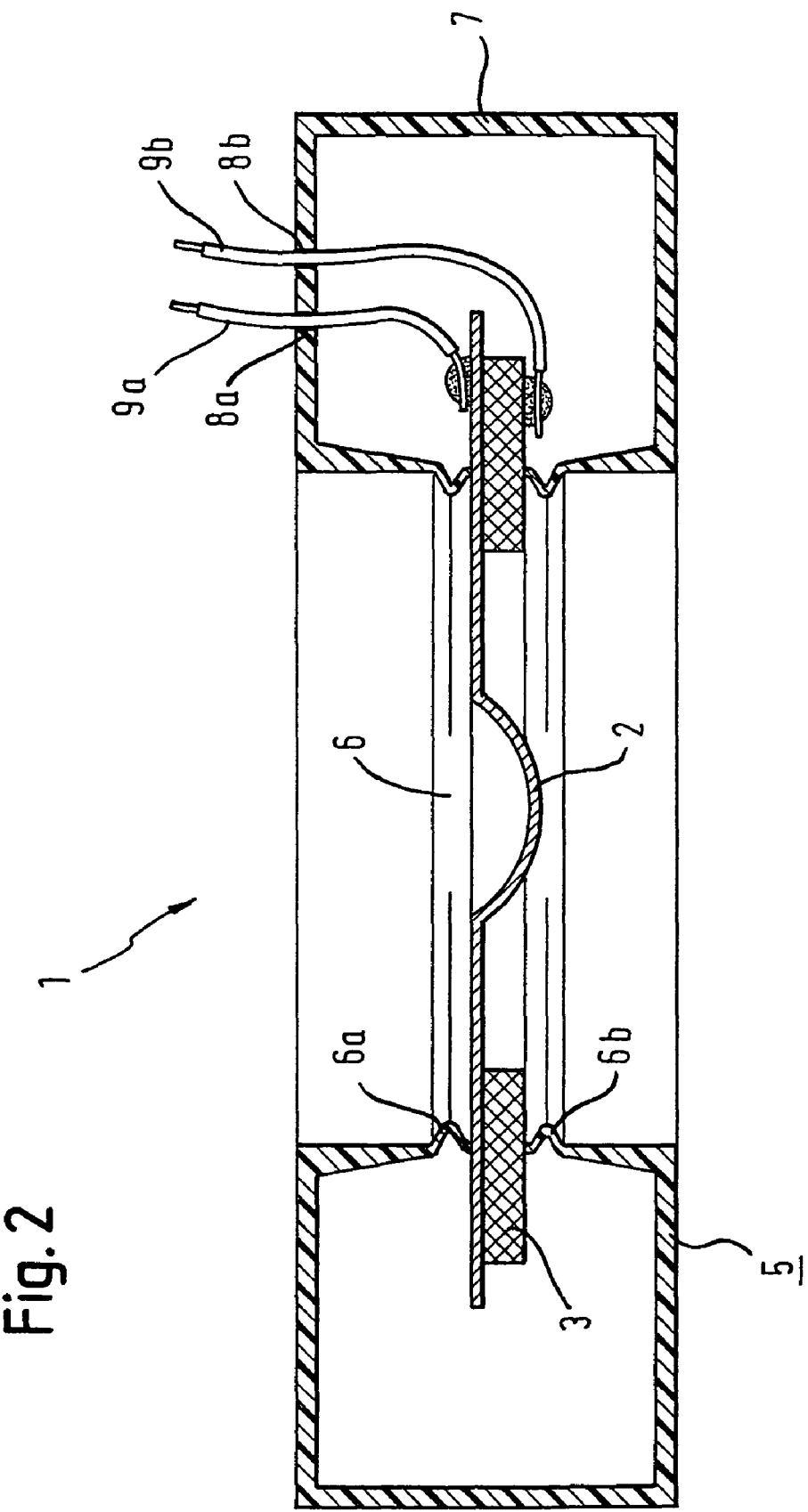
Figure 3:
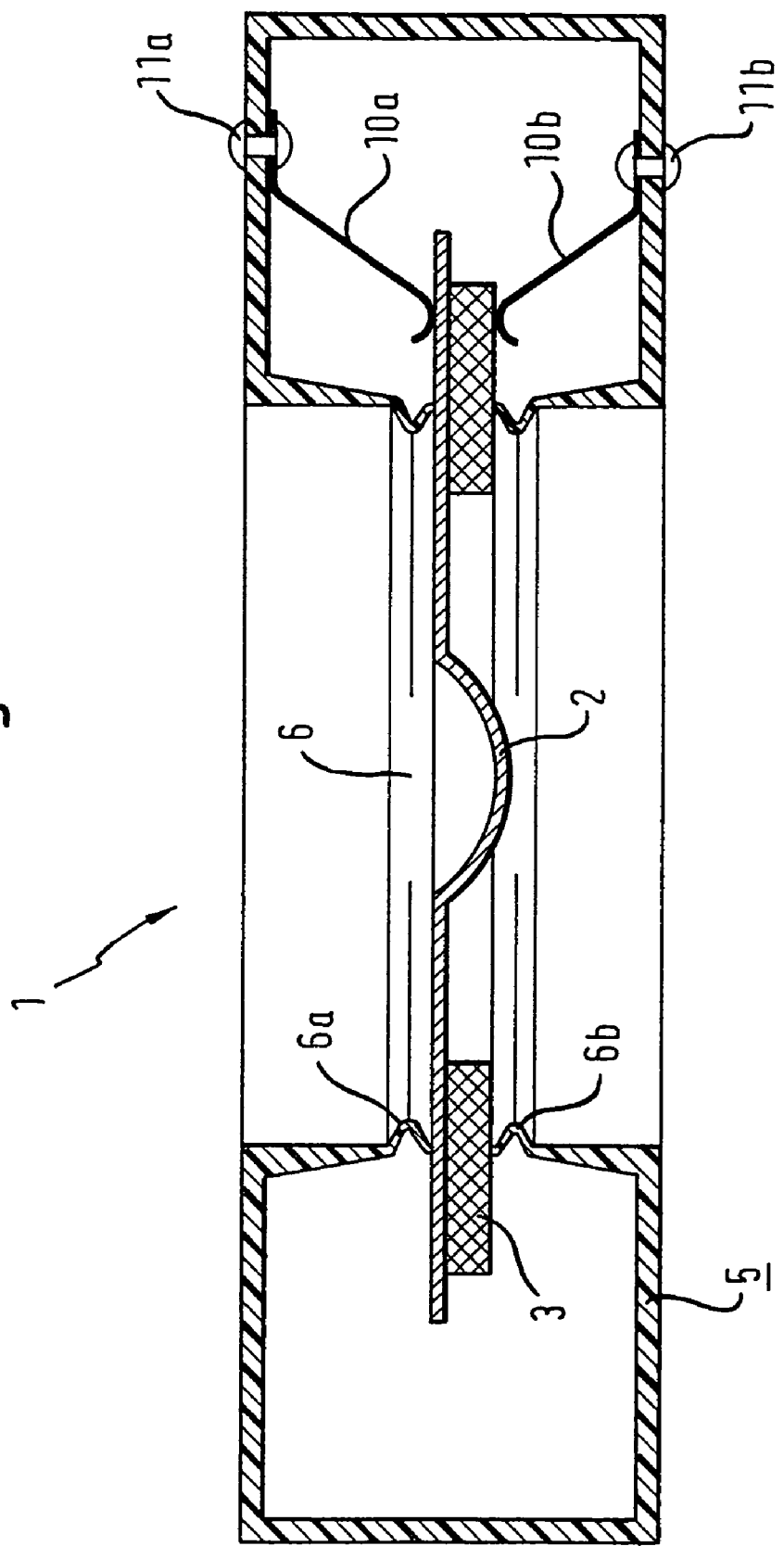
Figure 4:
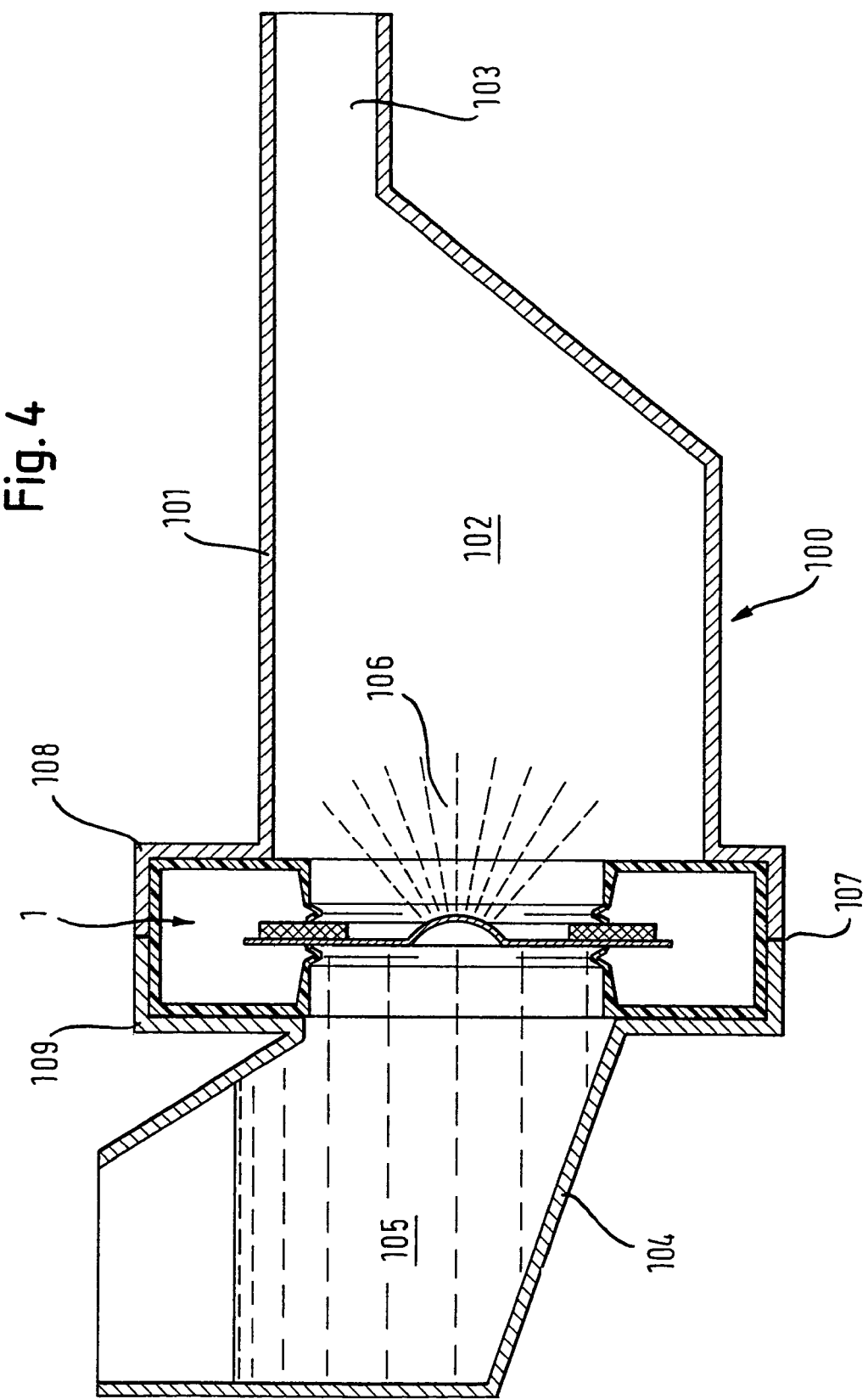
Figure 5:
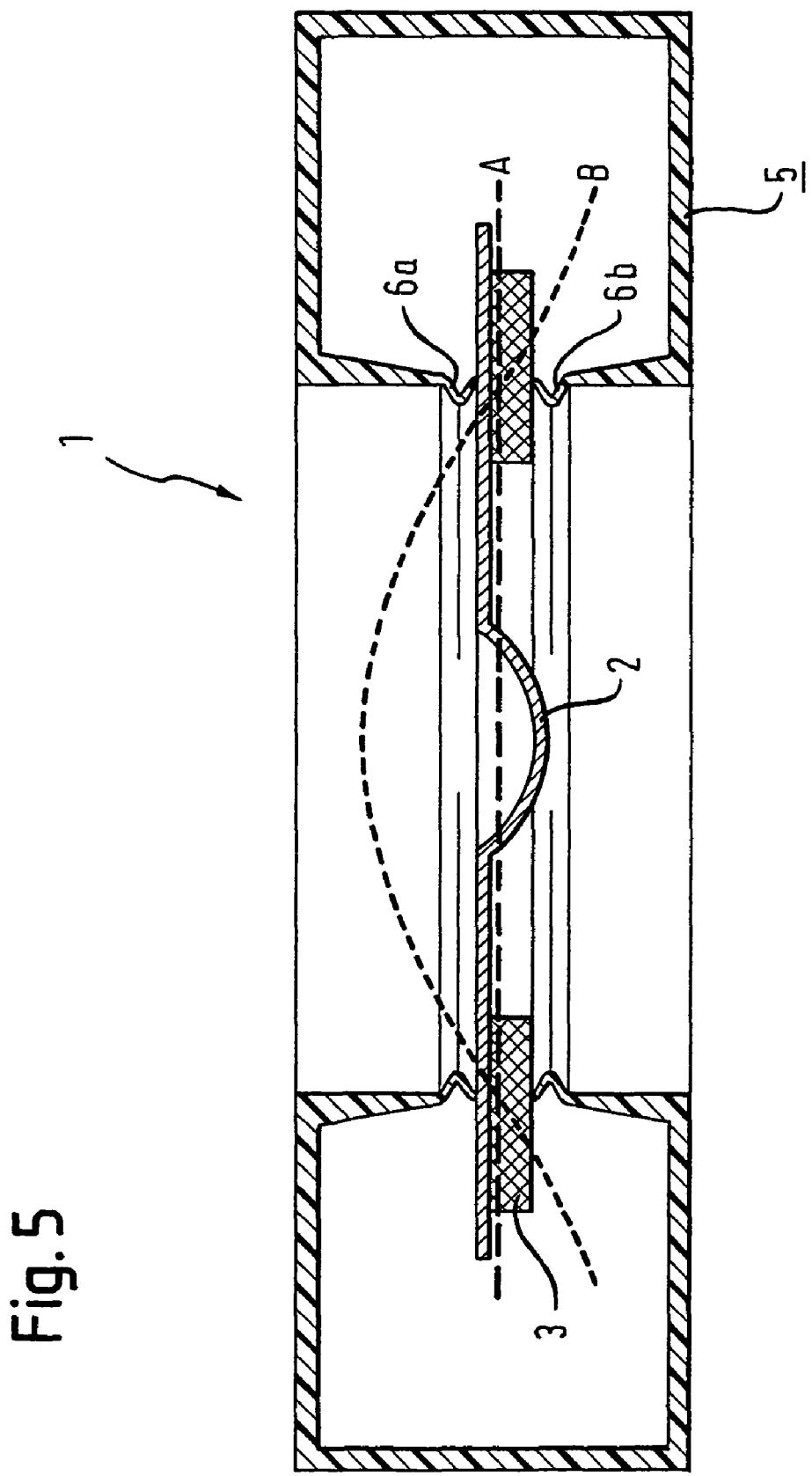

FIG. 1 shows a sectional perspective view of a first embodiment of an aerosol generating means according to the invention, FIG. 2 shows a sectional view of a second embodiment of an aerosol generating means according to the invention, FIG. 3 shows a sectional view of a third embodiment of an aerosol generating means according to the invention, FIG. 4 shows a sectional view of the arrangement of an aerosol generating means according to the invention in an example inhalation therapy device, and FIG. 5 shows a sectional view of a representation of oscillation states in an aerosol generating means according to the invention.

FIG. 1 shows a sectional perspective view of a first embodiment of an aerosol generating means 1 according to the invention. This embodiment comprises an oscillatable assembly having a membrane 2, an oscillation generator 3 and a substrate 4 to which the membrane 2 and the oscillation generator 3 are attached. However, in alternative designs, the oscillatable assembly can consist of just a membrane and an oscillation generator. It is characteristic of the oscillatable assembly of an aerosol generator according to the invention that the oscillation generator 3 can be controlled by an activation signal such that it causes the membrane 2 to oscillate so that a liquid present on a surface of the membrane is nebulised. A piezoelectric element, for example, comes into consideration as the oscillation generator 3, to which an electric activation signal can be supplied to cause oscillation.

It is provided in the shown embodiment according to FIG. 1 that the liquid is supplied on the concave side of the membrane 2 and is released as an aerosol on the convex side of the membrane 2 when the membrane 2 is caused to oscillate by the oscillation generating means 3. Both surfaces of the membrane 2 are exposed for this purpose, whereas other sections of the oscillatable assembly are disposed in the interior of an encapsulating means 5, which accommodates these areas of the oscillatable assembly. In the shown embodiment according to FIG. 1, the entire oscillation generator 3 and a large part of the substrate 4 are disposed in the interior of the encapsulating means 5.

At the sites where the oscillatable assembly penetrates the wall of the encapsulating means 5 and the oscillatable assembly 2, 3 contacts the encapsulating means 5, the encapsulating means 5 comprises a flexible passage which, in the embodiment shown according to FIG. 1, has flexible sealing lips 6*a* and 6*b*. Owing to the flexible sealing lips 6*a* and 6*b*, which touch the oscillatable assembly, mounting of the oscillatable assembly is achieved on the one hand, and on the other it is achieved that the interior of the encapsulating means 5 is closed, thereby protecting the sections of the oscillatable assembly disposed in the interior.

As can be seen from FIG. 1, the shape and size of the encapsulating means 5 is adapted to the oscillatable assembly. In the shown embodiment, which comprises a circular membrane 2, an annular oscillation generator 3 and an annular substrate 4, this means that the encapsulating means 5 is also designed in an annular manner. The membrane 2 is positioned in the opening of the annular encapsulating means 5 and is accessible such that liquid can be supplied and aerosol can be released.

An aerosol generator according to the invention can be handled as a whole with reduced risk for the oscillatable assembly since the parts which do not have to be exposed for the supply of liquid and release of aerosol are protected by the encapsulation. The encapsulated position of large parts of the oscillatable assembly has a particularly advantageous effect when cleaning the aerosol generator. However, contamination of the encapsulated areas of the oscillatable assembly cannot occur either when used in an inhalation therapy device. Despite encapsulation, the areas of the oscillatable assembly disposed in the interior of the encapsulating means according to the invention can oscillate virtually without being affected since the oscillatable assembly is only mounted at the flexible region 6*a*, 6*b* of the encapsulating means 5 and no further fixation of the oscillatable assembly, for example at the edge, is provided. In other words, the encapsulating means according to the invention combines effective protection of the oscillatable assembly with optimised mounting of the same.

In the embodiment shown in FIG. 1, the encapsulating means 5 comprises a casing 7, which is advantageously made of a comparatively hard material, for example a plastic, and flexible sealing lips 6a and 6b, which are attached to the casing 7 and form the flexible region of the encapsulating means 5. So that the oscillatable assembly can be inserted in the encapsulating means 5, the casing 7 of the embodiment according to FIG. 1 consists of two casing parts 7a and 7b, which are fitted together following insertion of the oscillatable assembly and are permanently joined with one another at the joining point 7c, for instance by means of gluing.

FIG. 2 shows a second embodiment of an aerosol generating means 1 according to the invention, which comprises an encapsulating means 5 as well as an oscillatable assembly. In the embodiment shown in FIG. 2, the oscillatable assembly comprises a membrane 2 and an oscillation generator 3, which is attached to the membrane 2. Parts of the membrane 2 and the oscillation generator 3 are positioned in an opening of the encapsulating means and are thus exposed so that a liquid can be supplied to the membrane 2 and an aerosol can be released. The remaining areas of the oscillatable assembly, in this embodiment the membrane 2 and the oscillation generator 3, are disposed in the interior of the encapsulating means 5, with the edge of the oscillatable assembly being able to oscillate in the interior of the encapsulating means 5 without being negatively affected, when, by activating the oscillation generator 3, the membrane 2 is caused to oscillate so as to generate an aerosol.

According to the invention, the encapsulating means 5 of the second embodiment comprises a passage 6 for passage of the oscillatable assembly through the wall of the encapsulating means 5. The passage 6 in the embodiment shown in FIG. 2 is realised in the form of flexible sealing lips 6*a* and 6*b*. The flexible sealing lips 6*a* and 6*b* lie on the membrane 2 and the oscillation generator 3 respectively, whereby the oscillatable assembly is supported by the flexible passage 6, i.e. by the flexible sealing lips 6*a* and 6*b*, of the encapsulating means 5. Owing to direct contact with the membrane 2 and the oscillation generator 3, the flexible sealing lips 6*a* and 6*b* at the same time ensure that the encapsulating means 5 is closed and that no substances can penetrate into the interior of the encapsulating means 5.

Contrary to the first embodiment according to FIG. 1, the flexible passage 6, i.e. the flexible sealing lips 6*a* and 6*b*, is configured integrally with the casing 7 of the encapsulating means 5 in the embodiment shown in FIG. 2. As is shown in FIG. 2, the sufficient flexibility of the flexible passage 6 is realised in this embodiment in that the wall thickness of the encapsulating means 5 is designed to be so thin in the region of the passage 6 that a flexible region is realised, which furthermore preferably has the form of curved sealing lips. In the remaining area of the casing 7, the encapsulating means otherwise advantageously has a wall thickness which provides sufficient stability to protect the parts of the oscillatable assembly positioned in the interior of the encapsulating means 5. The material from which the encapsulating means 5 according to the second embodiment as shown in FIG. 2 is made is preferably a plastic, a rubber or silicone. With these materials, the encapsulating means 5 can be configured in one piece since the elasticity of the material provides the entire structure with a sufficient amount of flexibility and elasticity, which enables the oscillatable assembly to be inserted in the passage 6, i.e. between the sealing lips 6*a* and 6*b*. If sufficient elasticity is not realizable, the casing 7 of the encapsulating means 5 according to the second embodiment can also be configured in two parts, as was described in connection with the first embodiment.

It is furthermore shown in FIG. 2 of the second embodiment of the invention, how electric supply leads 9*a* and 9*b* can be guided through openings 8*a* and 8*b* into the interior of the encapsulating means 5 in order to enable the supply of an activation signal to the oscillation generator 3.

FIG. 3 shows an alternative embodiment as regards the contacting of the oscillatable assembly. Reference is otherwise made to the description of the second embodiment. In the third embodiment of the invention according to FIG. 3, contacting of the oscillatable assembly occurs by means of contact springs 10*a* and 10*b*, which contact the oscillatable assembly. In the embodiment shown in FIG. 3, the first contact spring 10*a* contacts the membrane 2 and the second contact spring 10*b* contacts the oscillation generator 3. Since the membrane of an aerosol generator in question here is generally produced from a conductive material, an activation signal supplied via the contact spring 10*a* is relayed to the oscillation generator 3, for example a piezoelectric element. If a substrate is present, as is described in connection with the first embodiment, one of the contact springs can also be arranged such that it contacts the substrate which is generally also produced from a conductive material. If the membrane and/or substrate are not made from a conductive material, a connection can be established between the contact spring and the oscillation generator by means of through-connections through the membrane/substrate or by conductive coatings on the surface thereof.

The first and second contact springs 10*a* and 10*b* are mounted on the casing 7 of the encapsulating means 5, preferably through through-connections 11*a* and 11*b* which, in addition to mounting the contact springs 10*a* and 10*b*, also form the contact points for the contact springs that are accessible from the outside. An easily detachable electrical connection to control circuits accommodated in the inhalation therapy device can thereby be established in a simple manner when an aerosol generator according to the invention is inserted in an inhalation therapy device. Contact springs are advantageous with regard to production of the aerosol generator according to the invention since simple contacting when inserting the oscillatable assembly, in particular when inserting it into a two-part casing, is thereby possible.

FIG. 4 helps to explain the use of an aerosol generating means 1 according to the invention in a schematically shown inhalation therapy device 100, using as an example the design of the second and third embodiments, however without electric supply leads. The inhalation therapy device 100 comprises a first casing part 101, which accommodates a nebulising chamber 102 in its interior and comprises a mouthpiece 103, via which the patient inhales an aerosol generated into the nebulising chamber 102. The inhalation therapy device furthermore comprises a liquid container 104, in which a liquid 105 can be stored. The liquid 105 filled in the liquid reservoir 104 is disposed on one side of the membrane of the aerosol generator 1 according to the invention. When the membrane is caused to oscillate, an aerosol 106 is generated from the liquid 105, which enters the nebulising chamber 102 of the inhalation therapy device 100.

As is shown in FIG. 4, the inhalation therapy device 100 shown as an example can be separated into two casing parts 101 and 104 at a separation point 107. A first receptacle 108, which is configured integrally with the first casing part 101, and a second receptacle 109, which is configured integrally with the second casing part 104 of the inhalation therapy device 100, is disposed in this region. An aerosol generator 1 according to the invention is inserted into the receptacles 108 and 109 and the two parts of the casing are then connected together. The inhalation therapy device is then ready for use.

FIG. 5 shows an aerosol generating means 1 according to the invention having an encapsulating means 5 and an oscillatable assembly 2, 3. As regards the details hereof, reference is made to the detailed explanation of the three embodiments described above. The point at which the flexible passage 6 of the encapsulating means 5 advantageously contacts the oscillatable assembly is to be explained by means of FIG. 5. For this purpose, the position of the oscillatable assembly in its idle state is indicated in FIG. 5 by the dashed lined A, whereas the dashed line B indicates a deflected position of the oscillatable assembly. As is apparent from FIG. 5, the contact point of the sealing lips 6*a* and 6*b* of the encapsulating means 5 is in the region of an oscillation node or an oscillation nodal line. Owing to this advantageous arrangement of the contact point between the oscillatable assembly and the encapsulating means, the oscillation behaviour of the oscillatable assembly is virtually unaffected by the encapsulating means 5 since the contact with and mounting of the oscillatable assembly by the encapsulating means takes place at a point at which there is almost no movement.

The position of the oscillation nodal lines is dependent on the frequency of the activation signal and the structure of the oscillatable assembly. However, the encapsulating means 5 can in any case be designed such that the flexible region 6 of the encapsulating means 5 contacts and mounts the oscillatable assembly at an oscillation nodal line.

It must be noted with regard to FIG. 5 that the deflection of line B has been shown much larger than actually occurs for the purpose of clarification. Furthermore, it is obvious that several antinodes can also occur between the contact points if the oscillatable assembly is correspondingly activated.

The positioning of the contact points between the oscillatable assembly and the encapsulating means along an oscillation nodal line of the oscillatable assembly is a particularly advantageous design of the aerosol generating means according to the invention. If contact with and mounting of the oscillatable assembly occurs in this manner, optimal mounting is also ensured in addition to the encapsulating effects described above since the oscillating structure, namely the oscillatable assembly consisting of the membrane and oscillation generator and possibly a substrate, can oscillate virtually without being affected. This is because, on the one hand, oscillation of the oscillatable assembly is not affected as a result of mounting by the flexible region 6 of the encapsulating means 5. On the other hand, there is no bordering at the edge of the oscillatable assembly which can lead to a negative effect. Protection of at least parts of the oscillatable assembly, for example the contacting, is in any case always achieved by the encapsulating means, and thus an aerosol generating means having an optimally oscillating membrane and which is on the whole easy to handle is realised.

The invention claimed is:

1. An aerosol generating means for inhalation therapy devices, comprising:

an oscillatable assembly having a membrane, to which a liquid can be supplied for generation of an aerosol, and an oscillation generating means, by means of which the membrane can be caused to oscillate for generation of an aerosol;

an encapsulating means for accommodating and mounting the oscillatable assembly, the encapsulating means defining an interior such that at least part of the membrane and at least part of the oscillation generating means are disposed in the interior of the encapsulating means and at least another part of the membrane is exposed for supply of a liquid and generation of an aerosol, said encapsulating means having a passage, wherein the passage of the encapsulating means comprises at least two sealing lips, which contact the oscillatable assembly, wherein the encapsulating means comprises a casing and the at least two sealing lips, wherein the parts of membrane and the oscillation generating means disposed in the interior of the encapsulating means are protected by the encapsulating means against exposure to the liquid and the generated aerosol, and wherein the casing and the at least two sealing lips are formed integrally; and a housing having a receptacle configured to receive and mount the encapsulating means.

2. An aerosol generating means according to claim 1, wherein the passage of the encapsulating means contacts the oscillatable assembly in the region of an oscillation nodal line.

3. An aerosol generating means according to claim 1, wherein the passage is attached to the casing.

4. An aerosol generating means according to claim 1, wherein the casing is formed in two parts.

5. An aerosol generating means according to claim 1, wherein the encapsulating means comprises openings for electric supply leads.

6. An aerosol generating means according to claim 5, wherein the encapsulating means comprises electric supply leads and/or electric contact springs in its interior for supplying electric activation signals to the oscillatable assembly.

7. An aerosol generating means according to claim 6, wherein the supply leads are guided through the openings.

8. An aerosol generating means according to claim 6, wherein the electric contact springs are mounted by means of through-connections, which are disposed in the openings and form contact points on the outer surface of the encapsulating means.

9. An aerosol generator for inhalation therapy devices, comprising:

an oscillatable assembly having a membrane, to which a liquid can be supplied for generation of an aerosol, and an oscillation generator, by which the membrane can be caused to oscillate for generation of an aerosol;

a casing for accommodating and mounting the oscillatable assembly, the casing defining an interior such that at least part of the membrane and at least part of the oscillation generator are disposed in the interior of the casing and at least another part of the membrane is exposed for supply of a liquid and generation of an aerosol, said casing having a flexible passage, wherein the flexible passage of the casing comprises at least two flexible sealing lips, which contact the oscillatable assembly, wherein the parts of the membrane and the oscillation generator disposed in the interior of the casing are protected by the casing against exposure to the liquid and the generated aerosol, and wherein the flexible sealing lips and the casing are formed integrally of a flexible material; and a housing having a receptacle configured to receive and mount the casing.

* * * * *